US009251560B2

(12) United States Patent
Ishii et al.

(10) Patent No.: US 9,251,560 B2
(45) Date of Patent: Feb. 2, 2016

(54) MEDICAL IMAGE DIAGNOSIS APPARATUS AND PHASE DETERMINATION METHOD USING MEDICAL IMAGE DIAGNOSIS APPARATUS

(71) Applicants: Sunao Ishii, Tokyo (JP); Takayuki Kadomura, Tokyo (JP); Hirohisa Izumo, Tokyo (JP)

(72) Inventors: Sunao Ishii, Tokyo (JP); Takayuki Kadomura, Tokyo (JP); Hirohisa Izumo, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 38 days.

(21) Appl. No.: 14/360,148

(22) PCT Filed: Dec. 12, 2012

(86) PCT No.: PCT/JP2012/082138
§ 371 (c)(1),
(2) Date: May 22, 2014

(87) PCT Pub. No.: WO2013/094483
PCT Pub. Date: Jun. 27, 2013

(65) Prior Publication Data
US 2014/0307935 A1 Oct. 16, 2014

(30) Foreign Application Priority Data

Dec. 21, 2011 (JP) .................................. 2011-279100

(51) Int. Cl.
| G06K 9/00 | (2006.01) |
| G06T 3/00 | (2006.01) |
| A61B 6/03 | (2006.01) |
| A61B 6/02 | (2006.01) |
| A61B 6/00 | (2006.01) |

(52) U.S. Cl.
CPC ............... *G06T 3/0056* (2013.01); *A61B 6/032* (2013.01); *A61B 6/503* (2013.01); *A61B 6/5288* (2013.01); *A61B 6/027* (2013.01); *A61B 6/4078* (2013.01); *A61B 6/4233* (2013.01); *A61B 6/481* (2013.01); *G06T 2207/30048* (2013.01)

(58) Field of Classification Search
None
See application file for complete search history.

(56) References Cited

U.S. PATENT DOCUMENTS

2007/0030946 A1 2/2007 Tsuyuki et al.

FOREIGN PATENT DOCUMENTS

| JP | 2007-37782 | 2/2007 |
| JP | 2008-228829 | 10/2008 |
| JP | 2009-5789 | 1/2009 |

OTHER PUBLICATIONS

International Search Report in PCT/JP2012/082138.

*Primary Examiner* — Atiba O Fitzpatrick
(74) *Attorney, Agent, or Firm* — Cooper & Dunham LLP

(57) ABSTRACT

In order to provide a medical image diagnosis apparatus and a phase determination method using a medical image diagnosis apparatus that can determine an appropriate movement phase when obtaining a tomographic image corresponding to a specific movement phase, there are provided a storage unit that stores material distribution information, which is acquired from an object including a target organ that moves periodically, and movement information, which is measured together with the material distribution information, an image reconstruction unit that reconstructs a plurality of tomographic images of different movement phases using the material distribution information and the movement information, a superimposed image creation unit that creates a superimposed image by superimposing the plurality of tomographic images, a specific position calculation unit that calculates a specific position of the target organ based on the superimposed image, and a specific phase determination unit that determines a specific phase of the target organ based on the specific position.

10 Claims, 14 Drawing Sheets

MEDICAL IMAGE DIAGNOSIS APPARATUS AND PHASE DETERMINATION METHOD USING MEDICAL IMAGE DIAGNOSIS APPARATUS

TECHNICAL FIELD

The present invention relates to a medical image diagnosis apparatus including an X-ray computed tomography (CT) apparatus, and in particular, to a technique for performing scanning and image reconstruction of a moving organ, such as the heart.

BACKGROUND ART

When a moving organ is scanned by a medical image diagnosis apparatus represented by the X-ray CT apparatus, artifacts due to motion, so-called motion artifacts, are caused in the obtained tomographic image. As a method of reducing the motion artifacts, there is a method of controlling the acquisition timing of projection data or processing the acquired projection data based on electrocardiographic information or respiration information measured using a biometric sensor, such as an electrocardiograph or a respiratory sensor. With reference to the scanning of the heart as an example, there is a method in which electrocardiographic information measured using an electrocardiograph is collected together with projection data and projection data corresponding to an arbitrary cardiac phase is extracted from the collected projection data to perform image reconstruction and as a result, a tomographic image of the heart corresponding to the cardiac phase is obtained. This method is called an electrocardiographic synchronous reconstruction method.

In order to reduce the motion artifacts in the electrocardiographic synchronous reconstruction method, it is important to specify the cardiac phase corresponding to the projection data, which is used for image reconstruction, as an optimal phase, for example, as a cardiac phase in which the movement amount of the heart is smallest. PTL 1 discloses reconstructing a plurality of images of different cardiac phases, generating a plurality of difference images of different cardiac phases from the plurality of reconstructed images, and determining a specific cardiac phase based on the amount of movement corresponding to a plurality of cardiac phases calculated using the generated difference images. That is, a cardiac phase in which the sum of absolute values of the pixel values of the generated difference images is smallest is determined as a cardiac phase in which the amount of movement is small.

CITATION LIST

Patent Literature

PTL 1: JP-A-2007-37782

SUMMARY OF INVENTION

Technical Problem

In PTL 1, however, a specific cardiac phase is just determined based on the difference image generated between a plurality of images of different cardiac phases, and the influence of motion artifacts or noise, which is included in the respective images of different cardiac phases, on the determined cardiac phase is not taken into consideration. Since the amount of generation of motion artifacts or noise differs depending on an image, extra information, such as motion artifacts or noise, may be emphasized in the generated difference image. That is, a specific cardiac phase, which is determined based on the image in which motion artifacts or noise is emphasized, may not be an appropriate cardiac phase.

Therefore, it is an object of the present invention to provide a medical image diagnosis apparatus and a phase determination method using a medical age diagnosis apparatus that can determine an appropriate movement phase when obtaining a tomographic image corresponding to a specific movement phase.

Solution to Problem

In order to achieve the object described above, the present invention is a medical image diagnosis apparatus and a phase determination method using a medical image diagnosis apparatus for calculating a specific position based on a superimposed image, which is created using a plurality of tomographic images of different movement phases, and determining a specific movement phase based on the calculated specific position.

Specifically, there are provided: a storage unit that stores material distribution information, which is acquired from an object including a target organ that moves periodically, and movement information, which is measured together with the material distribution information; an image reconstruction unit that reconstructs a plurality of tomographic images of different movement phases using the material distribution information and the movement information; a superimposed image creation unit that creates a superimposed image by superimposing the plurality of tomographic images; a specific position calculation unit that calculates a specific position of the target organ based on the superimposed image; and a specific phase determination unit that determines a specific phase of the target organ based on the specific position.

In addition, a phase determination method using a medical image diagnosis apparatus includes: an image reconstruction step of reconstructing a plurality of tomographic images of different movement phases using material distribution information, which is acquired from an object including a target organ that moves periodically, and movement information, which is acquired together with the material distribution information; a superimposed image creation step of creating a superimposed image by superimposing the plurality of tomographic images; a specific position calculation step of calculating a specific position of the target organ based on the super imposed image; and a specific phase determination step of determining a specific phase of the target organ based on the specific position.

Advantageous Effects of Invention

According to the present invention, it is possible to provide a medical image diagnosis apparatus and a phase determination method using a medical image diagnosis apparatus that can determine an appropriate movement phase when obtaining a tomographic image corresponding to a specific movement phase.

DESCRIPTION OF EMBODIMENTS

Figure 1:
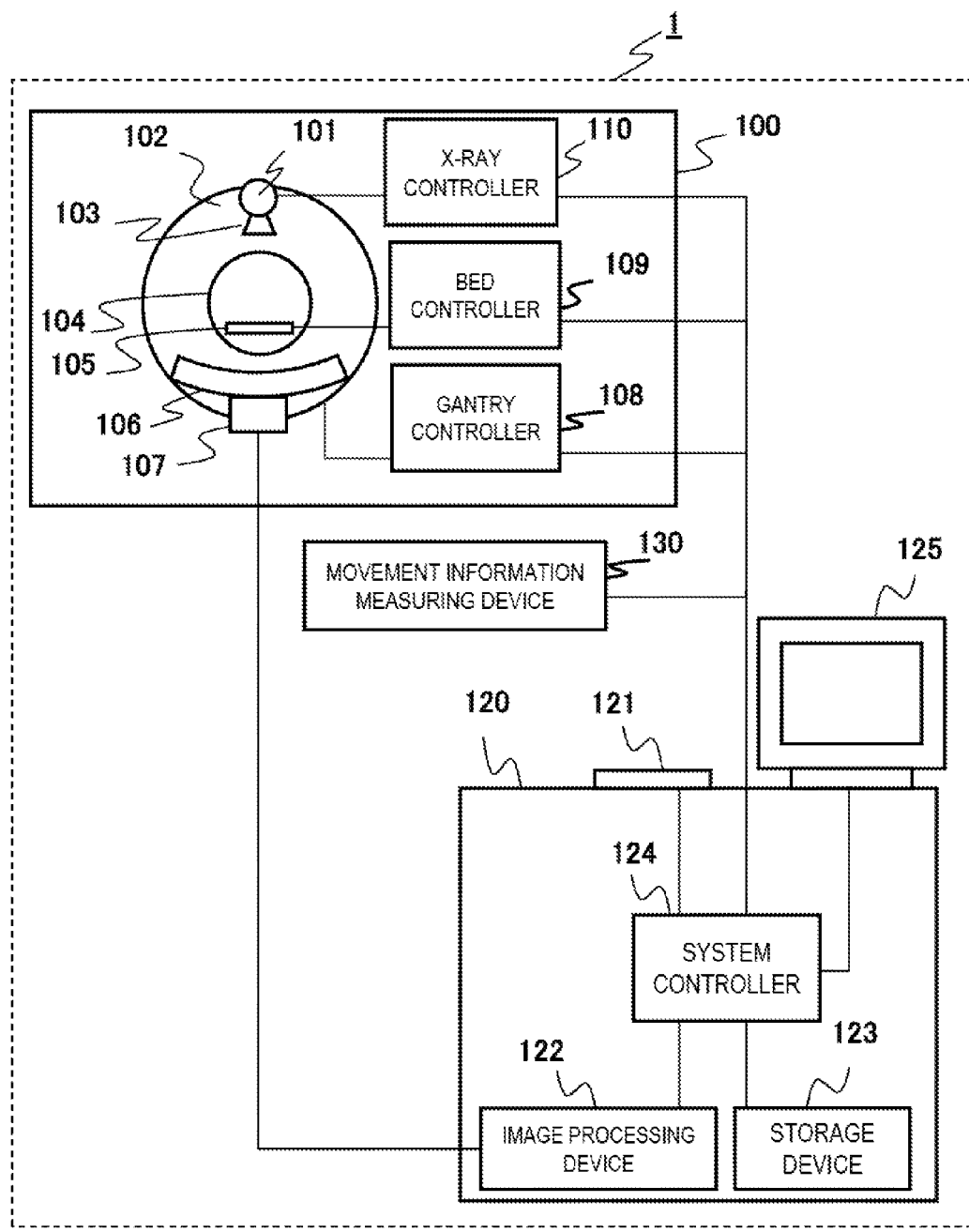
FIG. 1 is a block diagram showing the entire configuration of an X-ray CT apparatus of the present invention.

Hereinafter, preferred embodiments of an X-ray CT apparatus, which is one of a medical image diagnosis apparatus according to the present invention, will be described with reference to the accompanying diagrams. In the following explanation and the accompanying diagrams, the same reference numerals are given to components with the same functions, and repeated explanation thereof will be omitted.

FIG. 1 is a block diagram showing the entire configuration of an X-ray CT apparatus. As shown in FIG. 1, an X-ray CT apparatus 1 includes a scanning gantry unit 100, an operation unit 120, and a movement information measuring device 130.

The scanning gantry unit 100 includes an X-ray tube device 101, a rotary disk 102, a collimator 103, an X-ray detector 106, a data acquisition system 107, a bed device 105, a gantry controller 108, a bed controller 109, an X-ray controller 110, an input/output device 111, and an electrocardiographic data acquisition device 112.

The X-ray tube device 101 is a device that irradiates an object placed on the bed device 105 with X-rays. The collimator 103 is a device for limiting the irradiation range of X-rays irradiated from the X-ray tube device 101. The rotary disk 102 includes an opening 104 through which the object placed on the bed device 105 is inserted, and rotates around the object in a state where the X-ray tube device 101 and the X-ray detector 106 are mounted therein. The X-ray detector 105 is a device that disposed opposite the X-ray tube device 101 and measures the spatial distribution of transmitted X-rays by detecting X-rays transmitted through the object, and is formed by arraying a number of detection elements in a one-dimensional manner in the rotation direction of the rotary disk 102 or is formed by arraying a number of detection elements in a two-dimensional manner in the rotation direction and the rotation axis direction of the rotary disk 102. The data acquisition system 107 is a device that collects the amount of X-rays detected by the X-ray detector 106 as digital data. The gantry controller 108 is a device that controls the rotation and inclination of the rotary disk 102. The bed controller 109 is a device that controls up-and-down movement, back-and-forth movement, and left and right movement of the bed device 105. The X-ray controller 110 is a device that controls electric power input to the X-ray tube device 101.

The operation unit 120 includes an input device 121, an image processing device 122, a display device 125, a storage device 123, and a system controller 124. The input device 121 is a device for inputting the name of the object, examination date anal time, scanning conditions, and the like. Specifically, the input device 121 is a keyboard, a pointing device, a touch panel, or the like. The image processing device 122 is a device that reconstructs a CT image by performing arithmetic processing on the measurement data transmitted from the data acquisition system 107. The display device 125 is a device that displays the CT image created by the image processing device 122. Specifically, the display device 125 is a cathode-ray tube (CRT), a liquid crystal display, or the like. The storage device 123 is a device that stores data collected by the data acquisition system 107 and image data of the CT image created by the image processing device 122. Specifically, the storage device 123 is a hard disk drive (HDD) or the like. The system controller 124 is a device that controls these devices, the gantry controller 108, the bed controller 109, and the X-ray controller 110. In addition, the system controller 124 may execute the flow of a process, which will be described later.

The movement information measuring device 130 is a device that measures the movement information of an organ, which moves periodically, of the object. For example, the movement information measuring device 130 is an electrocardiograph or a respiratory sensor. The measurement result of the movement information measuring device 130 is transmitted to the system controller 124 and is stored in the storage device 123. When the movement information measuring device 130 is an electrocardiograph, electrocardiographic information is measured.

The X-ray controller 110 controls electric power input to the X-ray tube device 101 based on the scanning conditions input through the input device 121, in particular, based on an X-ray tube voltage, an X-ray tube current, and the like, so that the X-ray tube device 101 irradiates the object with X-rays corresponding to the scanning conditions. The X-ray detector 106 detects X-rays, which are emitted from the X-ray tube device 101 and transmitted through the object, using a number of X-ray detection elements and measures the distribution of transmitted X-rays. The rotary disk 102 is controlled by the gantry controller 108, and rotates based on the scanning conditions input through the input device 121, in particular, based on rotation speed and the like. The bed device 105 is controlled by the bed controller 109, and operates based on the scanning conditions input through the input device 121, in particular, based on a helical pitch and the like.

X-ray emission from the X-ray tube device 101 and the measurement of the distribution of transmitted X-rays by the X-ray detector 106 are repeated with the rotation of the rotary disk 102, and as a result, projection data from various angles is acquired. In the projection data, View showing each angle is matched with a channel (ch) number and a column number that are detection element numbers of the X-ray detector 106. At the same time as the acquisition of projection data, movement information is measured by the movement information measuring device 130. The acquired projection data from various angles is transmitted to the image processing device 122. The image processing device 122 reconstructs a CT image by performing back projection processing on the transmitted projection data from various angles. The CT image obtained by reconstruction is displayed on the display device 125.

The X-ray CT apparatus 1 may be connected to a server in a hospital or a server outside a hospital through a network (not shown), and may read required data timely from each server.

First Embodiment

Figure 2:
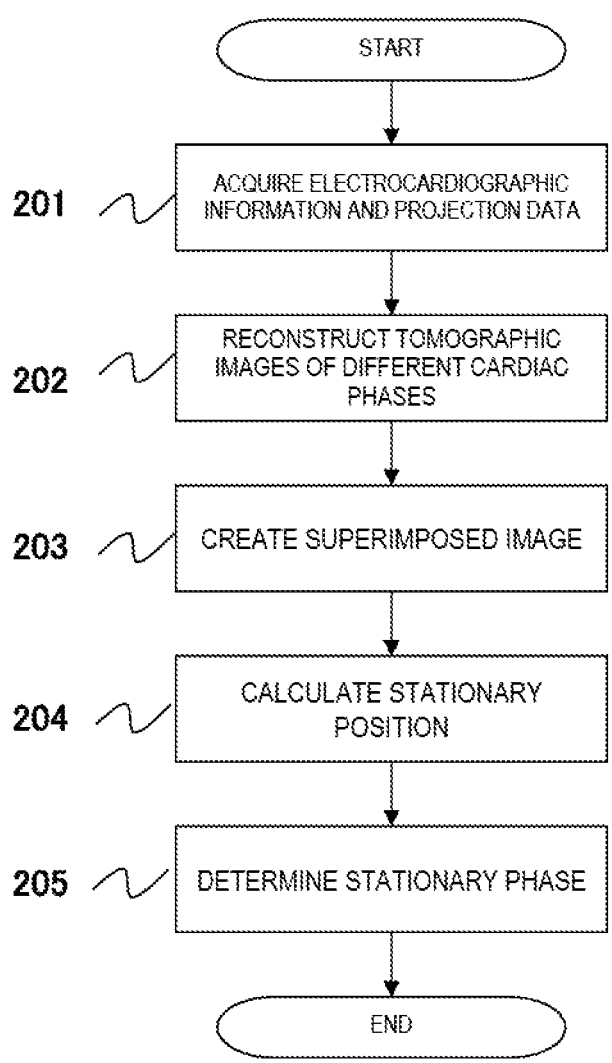
FIG. 2 is a diagram showing the process flow in a first embodiment of the present invention.

FIG. 2 is a diagram showing the flow of a process of a first embodiment of the present invention. Hereinafter, each step of FIG. 2 will be described in detail with reference to FIGS. 3 to 8. In addition, although a case where the heart including the coronary artery is a target organ will be described below, the target organ is not limited to the heart. For example, the target object may be an organ around the heart that moves according to the heart beat or may be an organ that moves according to the act of breathing.

In the present embodiment, since the heart is a target organ, movement information is electrocardiographic information. However, in the case of an organ that moves according to the act of breathing, respiratory information may be used as the movement information. In the present embodiment, a stationary position with less movement is calculated as a specific position of the target organ, and a stationary phase is determined as a specific phase of the target organ. However, the present invention is not limited to this.

(Step 201)

The system controller 124 reads electrocardiographic information 301 and projection data 302, which has been acquired together with the electrocardiographic information 301, from the storage device 123. The electrocardiographic information and the projection data may be read from a server in a hospital or a server outside a hospital through a network. The electrocardiographic information is measured by an electrocardiograph, which is the movement information measuring device 130, in parallel to the acquisition of the projection data 302. That is, the acquisition of the projection data 302 and the measurement of electrocardiographic information are performed simultaneously. When observing a blood vessel, it is preferable that projection data be acquired by contrast imaging.

Figure 3:
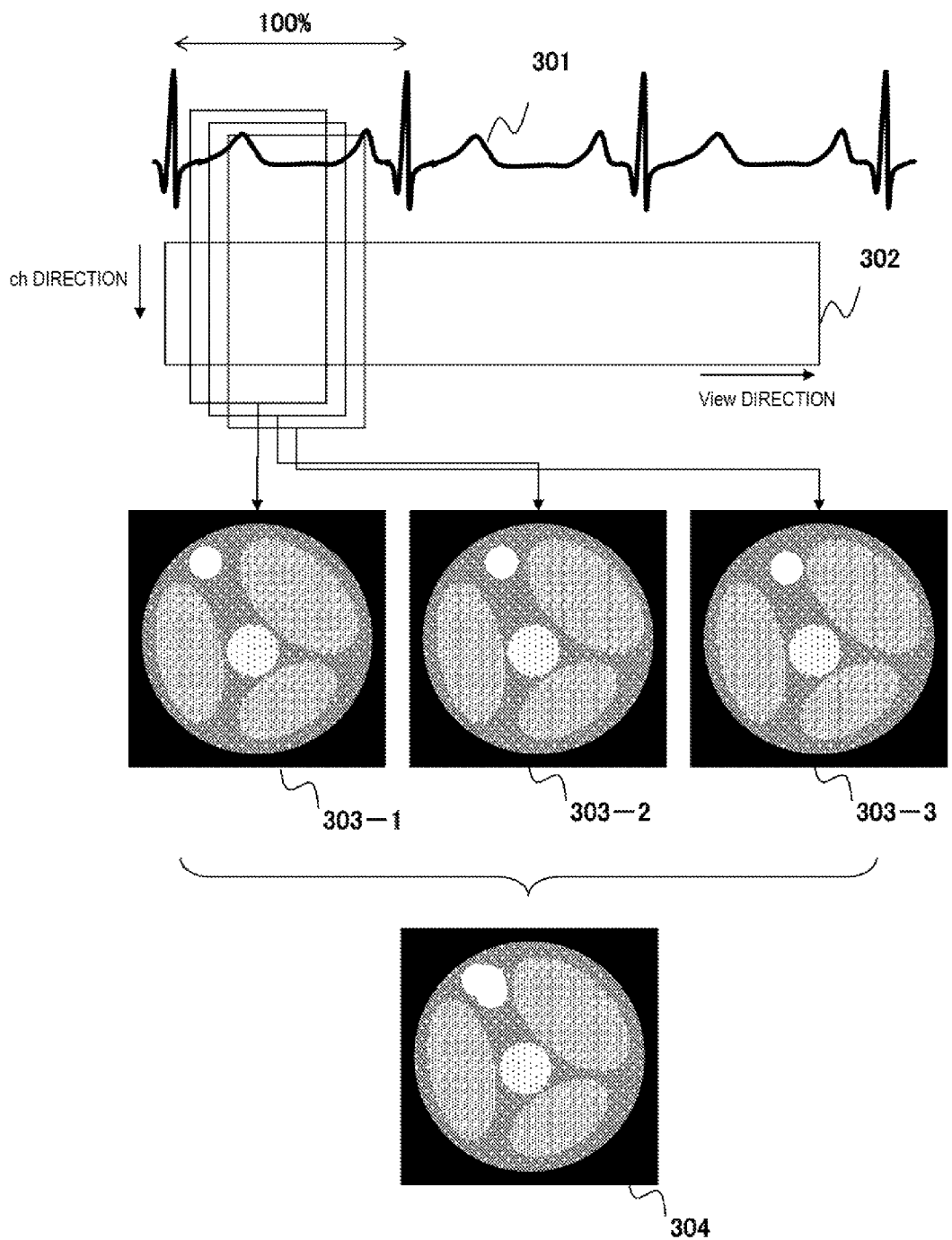
FIG. 3 is a diagram explaining the reconstruction of tomographic images of different cardiac phases and the creation of a superimposed image.

As shown in FIG. 3, the electrocardiographic information 301 and the projection data 302 are associated with the cardiac phase of the electrocardiographic information 301 and the view of the projection data 302. The cardiac phase is expressed by a relative value when the value between the adjacent P waves is assumed to be 100%.

(Step 202)

The system controller 124 causes the image processing device 122 to create tomographic images of different cardiac phases using the projection data 302 acquired together with the electrocardiographic information 301. For example, when a cardiac phase is set for each percentage, 100 tomographic images are created. It is preferable that tissue for comparison with the movement of the object be included in the tomographic images created in this step. For example, when observing the heart, it is preferable that coronary arteries be included in the tomographic images. In addition, since only the difference between the cardiac phases is compared, it is preferable that all parameters other than the cardiac phase be the same in the created tomographic images.

FIG. 3 shows three tomographic images 303-1 to 303-3 of different cardiac phases as a simulation diagram of the tomographic image of the heart. The tomographic images 303-1 to 303-3 shown in FIG. 3 are reconstructed using projection data acquired by contrast imaging, and the pixel value of the coronary artery displayed in the upper left part of each tomographic image is high compared with others.

(Step 203)

The system controller 124 causes the image processing device 122 to create a superimposed image using the tomographic images of different cardiac phases created in step 202. The superimposed image is an image created by integrating the pixel values of pixels of the same coordinates in a plurality of images. That is, the pixel value PVs (x, y) of the coordinates (x, y) in the superimposed image is calculated by the following expression.

$$PV_S(x, y) = \sum_{k=1}^{n} PV_k(x, y) \qquad \text{[Expression 1]}$$

Here, $PV_k$ (x, y) indicates a pixel value of the coordinates (x, y) in a tomographic image corresponding to the k-th cardiac phase, and n is the number of images used to create the superimposed image. FIG. 3 shows that a superimposed image 304 is created using the three tomographic images 303-1 to 303-3.

Motion artifacts or noise is included in the tomographic images of different cardiac phases, and the amount of occurrence changes with a tomographic image. However, the motion artifacts or noise included in each tomographic image is reduced by creating the superimposed image.

In the superimposed image, the trajectory of each organ in the tomographic image is displayed, and a portion with small movement is displayed brightly and a portion with large movement is displayed darkly. That is, the portion displayed brightly on the superimposed image is a position of small movement.

(Step 204)

Figure 4:
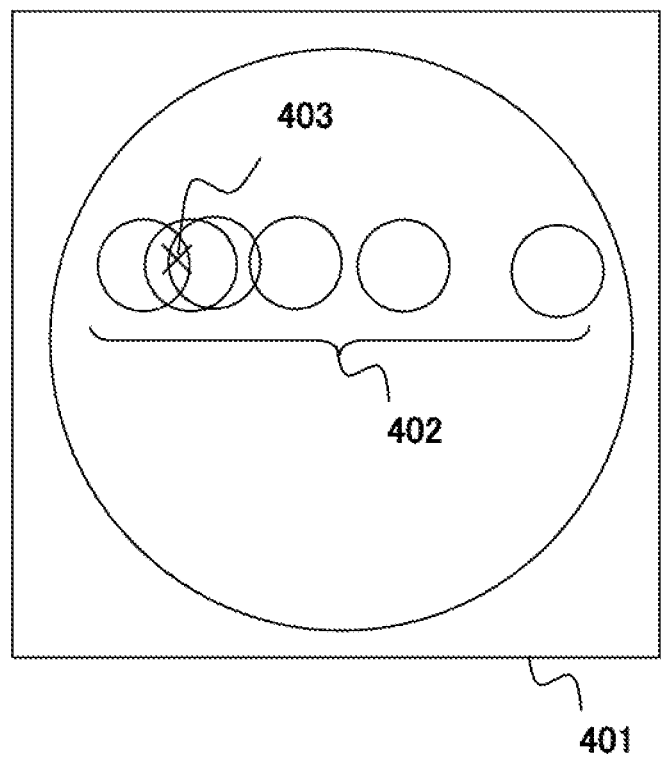
FIG. 4 is a diagram explaining the calculation of a stationary position.

The system controller 124 calculates the stationary position of the target organ based on the superimposed image created in step 203. The calculation of the stationary position will be described with reference to FIG. 4. FIG. 4 shows a superimposed image 401 as a simulation diagram of the superimposed image created in step 203. A trajectory 402 of the target organ is included in the superimposed image 401. Since the portion displayed brightly on the superimposed image 401 is a position with small movement as described previously, the brightest pixel in the trajectory 402 of the target organ is calculated as a stationary position 403. When there is a plurality of brightest pixels, the center-of-gravity coordinates of the plurality of pixels are calculated as the stationary position 403. In FIG. 4, a marker indicating the stationary position 403 is shown as X.

(Step 205)

The system controller 124 determines the stationary phase of the target organ based on the stationary position calculated in step 204. The determination of the stationary phase will be described with reference to FIG. 5.

Figure 5:
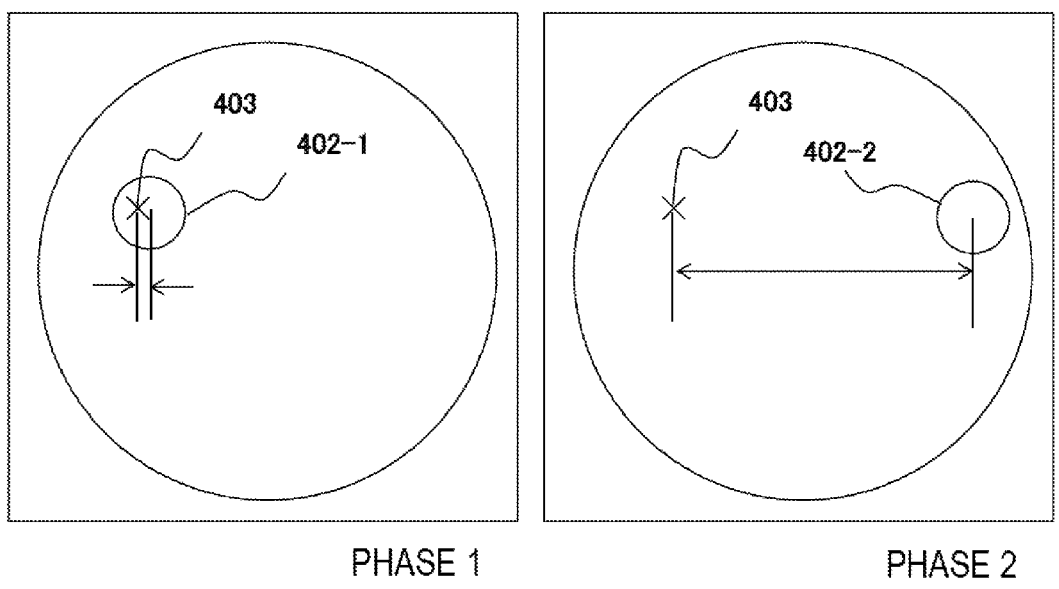
FIG. 5 is a diagram explaining the determination of a stationary phase.

In this step, first, a region showing the target organ is extracted on respective tomographic images of different cardiac phases. For region extraction, for example, threshold value processing is used. If the target organ is a contrast blood vessel, extraction is simple since the pixel value is high compared with other regions. FIG. 5 shows tomographic images of phase 1 and phase 2 as an example of tomographic images of different cardiac phases, and regions 402-1 and 402-2 showing the target organ are shown on the respective tomographic images.

A distance between a region of the target organ extracted and the stationary position 403 calculated in step 204 is measured. Distance measurement is executed for each of the tomographic images of different cardiac phases. As a result, a distance is calculated for each cardiac phase. In FIG. 5, a distance between the region 402-1 and the stationary position 403 and a distance between the region 402-2 and the stationary position 403 are shown on the tomographic images of the phase 1 and the phase 2, respectively.

Then, a stationary phase is determined based on the distance calculated for each cardiac phase. For example, a cardiac phase of the tomographic image with the shortest distance is determined as the stationary phase. In FIG. 5, the distance in the phase 1 is shorter than that in the phase 2. Accordingly, the phase 1 is determined as a stationary phase. In addition, it may be possible to approximate the relationship between the cardiac phase and the distance with a polynomial curve and determine the value of the cardiac phase, in which the value of the distance is a minimum value, as a stationary phase.

By executing the flow of the process described above, a specific position is calculated based on the superimposed mage created using a plurality of tomographic images of different movement phases, and a specific movement phase is determined based on the calculated specific position. According to this method, even if motion artifacts or noise is included in a plurality of tomographic images of different movement phases, the influence of the motion artifacts or noise is reduced by creating the superimposed image. Therefore, it is possible to determine an appropriate movement phase.

Figure 6:
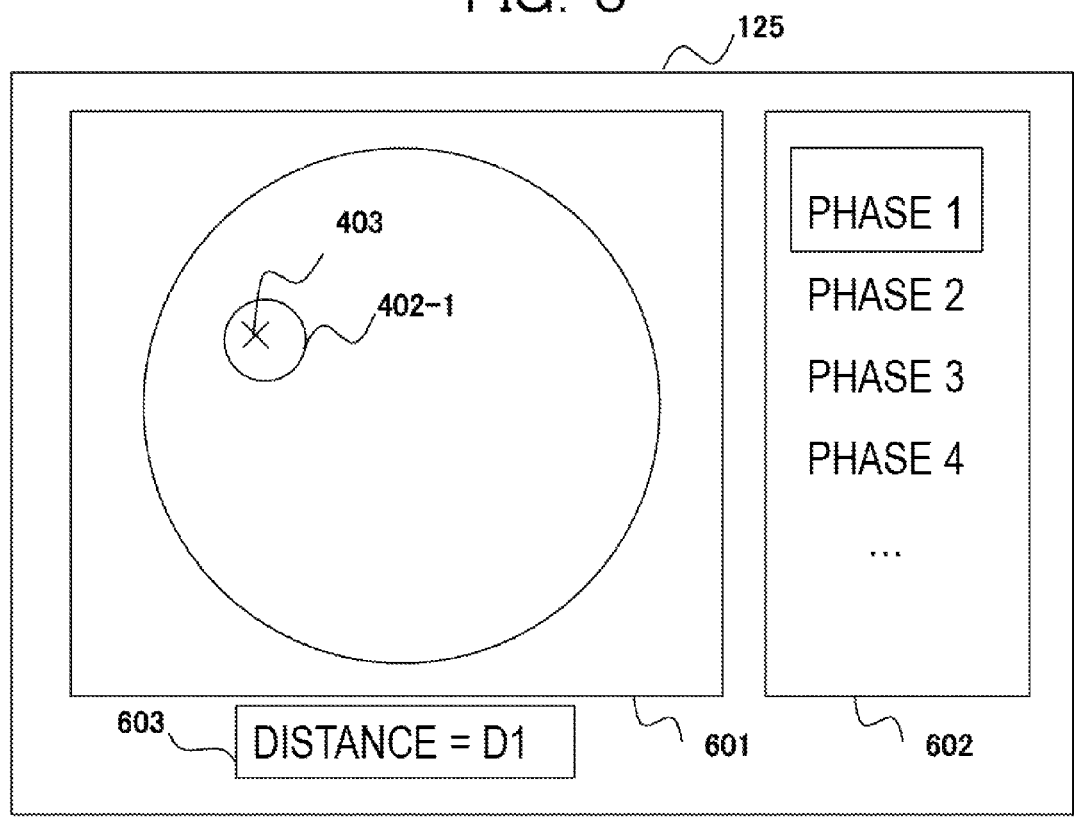
FIG. 6 is a diagram showing an example of a display screen in the first embodiment.

A screen for the operator to check the stationary phase determined in step 205 may be displayed on the display device 125. FIG. 6 shows an example of the display screen. The display screen shown in FIG. 6 includes an image display portion 601, a phase display portion 602, and a distance display portion 603.

One of a plurality of tomographic images of different cardiac phases is displayed on the image display portion 601 together with a marker indicating the stationary position 403 calculated in step 204. In FIG. 6, a tomographic image when the cardiac phase is the phase 1 is displayed, and the extracted target organ 402-1 and the marker indicating the stationary position 403 are displayed on the tomographic image.

The tomographic image displayed in the image display portion 501 may be a cine display. That is, a plurality of tomographic images of different cardiac phases may be sequentially switched and displayed while always displaying the marker indicating the stationary position 403. The display speed of the cine display does not necessarily need to be constant, and may be increased or decreased for an arbitrary cardiac phase. For example, the image update rate may be reduced before and after mid-diastole. In addition, the superimposed image 401 shown in FIG. 4 may be displayed in the image display portion 601 together with a marker.

Cardiac phases corresponding to respective tomographic images are displayed as a list in the phase display portion 602. In the list, a cardiac phase corresponding to the tomographic image displayed in the image display portion 601 or the stationary phase determined in step 205 is highlighted. In FIG. 6, since the cardiac phase of the tomographic image displayed on the image display portion 601 is the phase 1, the phase 1 is displayed so as to be enclosed in a box. As a form of highlighting, monochrome highlighting, colored highlighting, blinking display, and the like may be used. When a tomographic image is cine-displayed in the image display portion 601 or when a superimposed image is displayed, the stationary phase is preferably highlighted.

In the distance display portion 603, a distance between the stationary position 403 and the target organ on the tomographic image displayed in the image display portion 601 is numerically displayed. In FIG. 6, since the cardiac phase of the tomographic image displayed on the image display portion 601 is the phase 1, a distance between the target organ 402-1 and the stationary position 403 is displayed. In addition, when the tomographic image is cine-displayed in the image display portion 601, the value of the distance may be updated whenever the tomographic image changes. When a superimposed image is displayed in the image display portion 601, a distance at the time of stationary phase may be displayed.

When the operator selects one cardiac phase from the cardiac phase list displayed in the phase display portion 602 using the input device 121, a tomographic image corresponding to the selected cardiac phase may be displayed in the image display portion 601.

Figure 7:
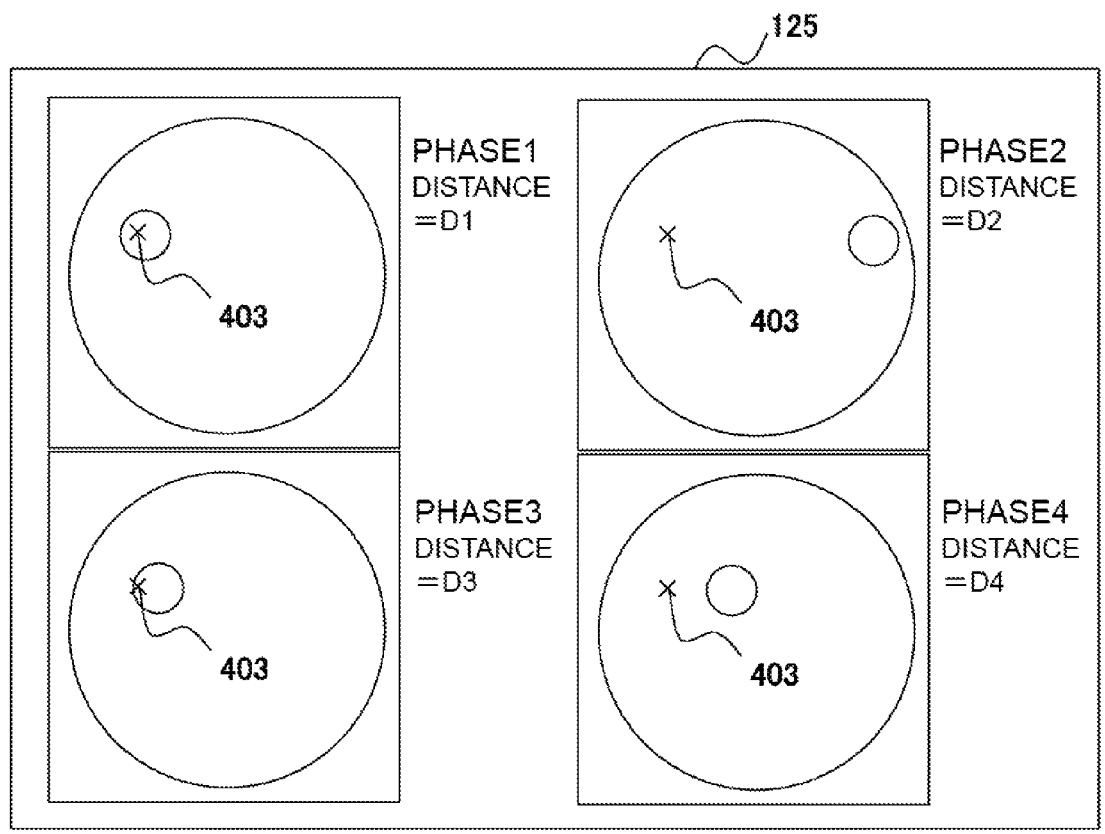
FIG. 7 is a diagram showing another example of the display screen in the first embodiment.
Figure 8:
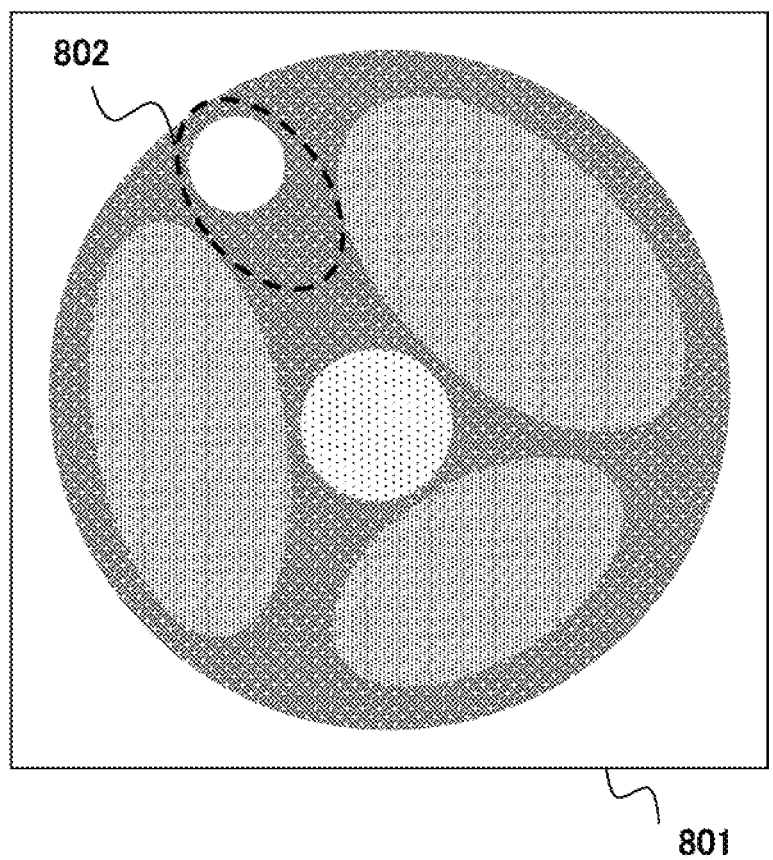
FIG. 8 is a diagram showing an example of the setting of an area of interest.

FIG. 7 shows another example of the display screen. In the display screen shown in FIG. 7, as an example in which a plurality of tomographic images of different cardiac phases are displayed, tomographic images of four cardiac phases are displayed together with a marker indicating the stationary position 403. A cardiac phase corresponding to each tomographic image and a distance between the stationary position 403 and the target organ on the tomographic image are displayed beside each tomographic image.

When creating a superimposed image in step 203, the calculation region may be limited. That is, a superimposed image may be created only in a region of interest 802 that the operator sets on a tomographic image 801 shown in FIG. 8 using the input device 121. Since the speed of processing can be increased by limiting the calculation region and there is no influence by regions outside the calculation region in subsequent steps, it is possible to improve the calculation accuracy in the calculation of the stationary position and the determination of the stationary phase. Even if the target organ moves to the outside of the region of interest 802 in some cardiac phases, the influence of the calculation accuracy on the stationary position is small since the movement can be considered to be large in the cardiac phases.

Prior to creating the superimposed image in step 203, it may also be possible to create a binary image, which is obtained by extracting only the target organ in each of tomographic images of different cardiac phases, and create a superimposed image using the binary image. By using the binary image, it is possible to reduce the influence of those other than the target organ.

Second Embodiment

In the first embodiment, the case of creating a superimposed image using tomographic images of different cardiac phases as they are in step 203 has been described. In the present embodiment, a superimposed image that is different from that of the first embodiment is created. That is, a superimposed image is created after multiplying each of the tomographic images of different cardiac phases by the weighting factor. Since the process flow of the present embodiment is the same as in the first embodiment except for step 203, step 203 of the present embodiment will be described below.

Figure 9:
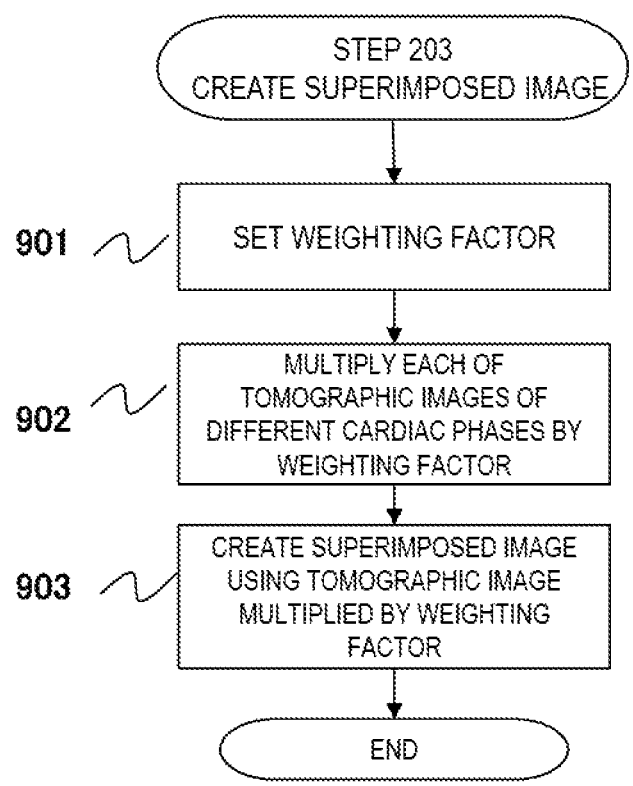
FIG. 9 is a diagram showing the process flow of step 203 in a second embodiment of the present invention.

FIG. 9 is a diagram showing the process flow of step 203 of a second embodiment of the present invention. Hereinafter, each step in FIG. 9 will be described in detail.

(Step 901)

The system controller 124 sets a weighting factor. The weighting factor is set for each cardiac phase, and the value between 0 and 1 is set in many cases.

Figure 10:
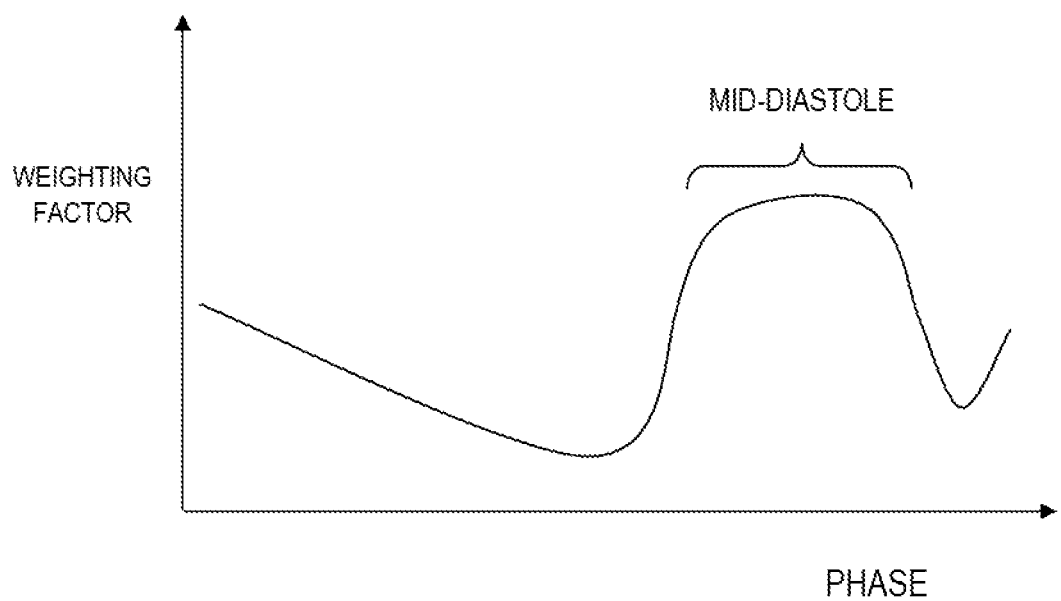
FIG. 10 is a diagram showing an example of a weighting factor.

FIG. 10 shows an example of the weighting factor. Generally, it is said that the movement of the organ according to the heart beat is small in the mid-diastole of the heart. Therefore, in FIG. 10, the weighting factor is set to be large in the cardiac phase of the mid-diastole. More extremely, the weighting factor may be set to 1 only in the range of the mid-diastole, and the weighting factor may be set to 0 in the other range.

Figure 11:
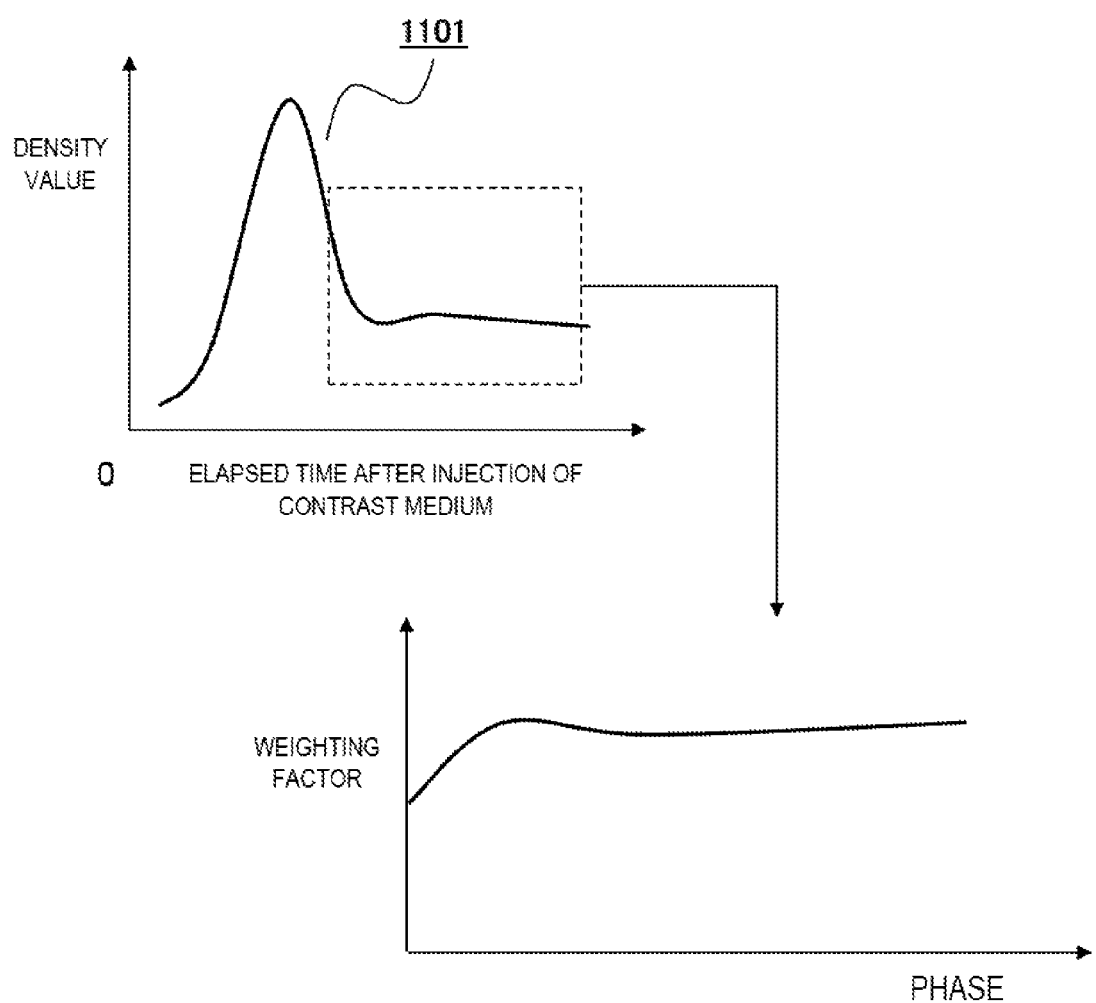
FIG. 11 is a diagram showing another example of the weighting factor.

FIG. 11 shows another example of the weighting factor. In a tomographic image obtained by contrast imaging, a pixel value may be different, even for the same blood vessel, according to the elapsed time after injection of a contrast medium. That is, when the target organ is a blood vessel, it is preferable to reduce the influence of the change in the pixel value according to the elapsed time after injection of a contrast medium. Incidentally, in contrast imaging, in order to measure the flow rate of the contrast medium before main imaging, a prescan called a monitoring scan is performed, and a time density curve (TDC) shown by the reference numeral 1101 in FIG. 11 is acquired. Therefore, in FIG. 11, a weighting factor is set based on the time density curve acquired by the monitoring scan. For example, if a curve in a range surrounded by the dotted line portion of the time density curve corresponds to the cardiac phase at the time of contrast imaging, a weighting factor is set using the curve of the dotted line portion. In the weighting curve shown in the lower right of FIG. 11, the inverse of the density value of the curve of the dotted line portion is set as a weighting factor, and is assigned to each cardiac phase.

(Step 902)

The system controller 124 causes the image processing device 122 to multiply each of the tomographic images of different cardiac phases by the weighting factor. In this step, the weighting factor set for each cardiac phase in step 901 is used.

(Step 903)

The system controller 124 causes the image processing device 122 to create a superimposed image using the tomographic image multiplied by the weighting factor. The calculation performed in steps 902 and 903 is expressed by the following expression.

$$PVs(x, y) = \sum_{k=1}^{n} (w_k \cdot PV_k(x, y))$$ [Expression 2]

Here, PVs (x, y) indicates a pixel value of the coordinates (x, y) in a superimposed image, $w_k$ indicates a weighting factor by which a tomographic image corresponding to the k-th cardiac phase is multiplied, $PV_k$ (x, y) indicates a pixel value of the coordinates (x, y) in the k-th image, and n is the number of images used to create the superimposed image.

By executing the process flow described above, superimposed image is created after multiplying each of the tomographic images of different cardiac phases by the weighting factor. By executing such processing, it is possible to create a superimposed image, in which the range of a specific cardiac phase is highlighted, or a superimposed image, in which a difference caused between cardiac phases is reduced. For example, when the weighting factor is set to 1 in the range of the mid-diastole and to 0 in the other range, only the tomographic image corresponding to the range of the mid-diastole is used to create the superimposed image. Therefore, it is possible to calculate a stationary position only in the range of the mid-diastole. In addition, when the weighting factor is set based on the time density curve shown in FIG. 11, a tomographic image in which the change in the pixel value according to the elapsed time after injection of a contrast medium is suppressed is used to create a superimposed image. Therefore, it is possible to improve the calculation accuracy of the stationary position.

Third Embodiment

In the first embodiment, the case of creating a superimposed image using tomographic images of different cardiac phases as they are in step 203 has been described. In the present embodiment, a superimposed image that is different from that in the first embodiment is created. That is, an interpolation image is created between tomographic images of different cardiac phases, and a superimposed image is created using the tomographic images of different cardiac phases and the interpolation image. Since the process flow of the present embodiment is the same as in the first embodiment except for step 203, step 203 of the present embodiment will be described below.

Figure 12:
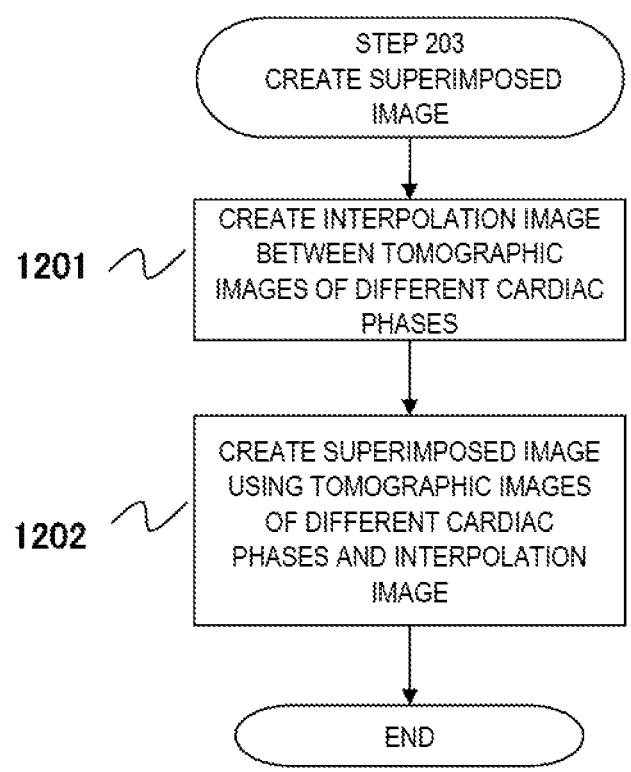
FIG. 12 is a diagram showing the process flow of step 203 in a third embodiment of the present invention.

FIG. 12 is a diagram showing the process flow of step 203 of the third embodiment of the present invention. Hereinafter, each step in FIG. 12 will be described in detail.

(Step 1201)

The system controller 124 causes the image processing device 122 to create an interpolation image between tomographic images of different cardiac phases. For example, an interpolation image corresponding to the cardiac phase in the middle of adjacent cardiac phases is created using the respective tomographic images corresponding to the adjacent cardiac phases. The number of interpolation images corresponding to the middle cardiac phase is smaller than the number of tomographic images of different cardiac phases by 1.

In addition, interpolation images created in this step are not limited to the interpolation image corresponding to the cardiac phase in the middle of adjacent cardiac phases. For example, it may also be possible to create interpolation images corresponding to cardiac phases that divide a region between the adjacent cardiac phases into three or more parts. In addition, preferably, the interval between the cardiac phase, to which the tomographic image created in step 202 corresponds, and the cardiac phase, to which the interpolation image corresponds, is an equal interval. For example, when an interpolation image is created by dividing a region between adjacent cardiac phases into three parts, it is preferable that a tomographic image, an interpolation image, an interpolation e, a tomographic image, an interpolation image, an interpolation image, a tomographic image, . . . be arranged in this order in a direction of the cardiac phase and the cardiac phase width between the respective images be equal.

The number of tomographic images used to create an interpolation image not limited to two tomographic images corresponding to adjacent cardiac phases, and three or more tomographic images may be used.

(Step 1202)

The system controller 124 causes the image processing device 122 to create a superimposed image using the tomographic images of different cardiac phases and the interpolation image created in step 1201. That is, the superimposed image is created by integrating all of the tomographic images created in step 202 and the interpolation image created in step 1201.

By executing the process flow described above, a superimposed image is created using the tomographic images of different cardiac phases and the interpolation image created between the tomographic images. By executing such processing, even if overlap does not occur in the target organ only with tomographic images of different cardiac phases, it is possible to accurately calculate the stationary position. That is, in the present invention, since a portion of the target organ where the overlap of the target organ is large is calculated as a stationary position, the stationary position may not be able to be accurately calculated unless overlap occurs in the target organ. Even in this case, it is possible to accurately calculate the stationary position by applying the present embodiment.

Fourth Embodiment

In the first embodiment, the case of creating a superimposed image using tomographic images of different cardiac phases as they are in step 203 has been described. In the present embodiment, a superimposed image that is different from that in the first embodiment is created. That is, an average image is created from a superimposed image that is created using tomographic images of different cardiac phases as they are, a difference image between the average image and the tomographic image of an arbitrary cardiac phase is created, and the difference image is replaced with the superimposed image. Since the process flow of the present embodiment is the same as in the first embodiment except for step 203, step 203 of the present embodiment will be described below.

Figure 13:
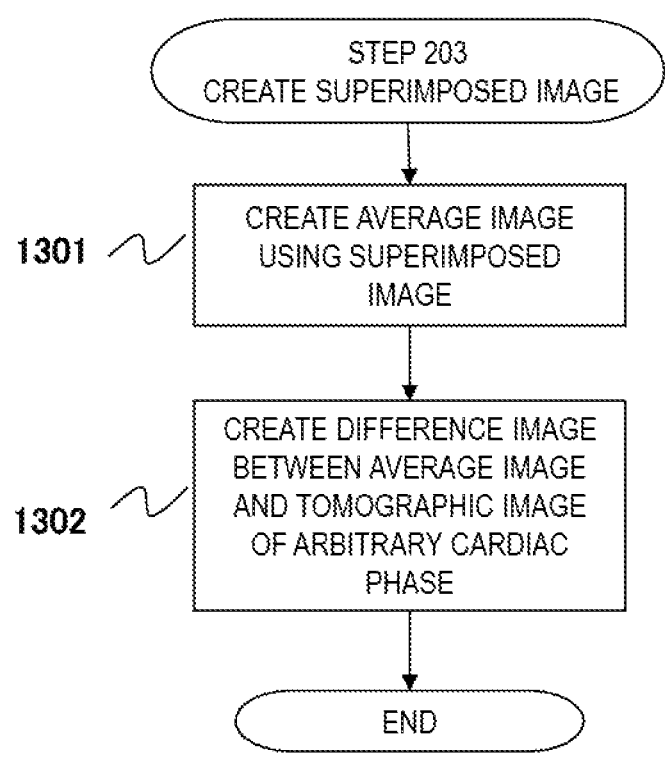
FIG. 13 is a diagram showing the process flow of step 203 in a fourth embodiment of the present invention.

FIG. 13 is a diagram showing the process flow of step 203 of the fourth embodiment of the present invention. Hereinafter, each step in FIG. 13 will be described in detail.

(Step 1301)

The system controller 124 causes the image processing device 122 to perform a process of creating an average image from a superimposed image that is created using tomographic images of different cardiac phases as they are. The pixel value PVa (x, y) of the coordinates (x, y) in the average image is calculated by the following expression.

$$PVa(x, y) = \frac{1}{n}\sum_{k=1}^{n} PV_k(x, y)$$ [Expression 3]

Here, $PV_k$ (x, y) indicates a pixel value of the coordinates (x, y) in a k-th image, and n is the number of images used to create the superimposed image.

(Step 1302)

The system controller 124 causes the image processing device 122 to create a difference image using the average image created in step 1301 and the tomographic image of an arbitrary cardiac phase. The pixel value PVd (x, y) of the coordinates (x, y) in the difference image is calculated by the following expression.

$$PVd(x,y)=PVa(x,y)-PV_k(x,y)$$ [Expression 4]

The difference image created in this step is replaced with the superimposed image created previously. That is, in step 204, the stationary position of the target organ is calculated based on the difference image created in this step.

In addition, the difference image created in this step may be a difference between a superimposed image, which is created using tomographic images of different cardiac phases as they are, and an image, which is n times a tomographic image of an arbitrary cardiac phase. The pixel value calculated in this case is n times the pixel value calculated by Expression 4. However, when calculating the stationary position in step 204, the relative comparison of the pixel values on the difference image is performed. Therefore, even if the pixel value becomes n times, there is no influence on the calculation accuracy of the stationary position.

By executing the process flow described above, a difference image between the average image, which is created from the superimposed image created using the tomographic images of different cardiac phases as they are, and the tomographic image of an arbitrary cardiac phase is created, and the difference image is replaced with the superimposed image. By executing such processing, even if the pixel value of the target organ is not sufficiently high compared with others, it is possible to accurately calculate the stationary position. That is, if the pixel value of the target organ is not sufficiently high compared with others, the stationary position may not be able to be accurately calculated due to the influence of organs with less movement over the entire cardiac phase. Even in this case, since the influence of organs with less movement over the entire cardiac phase is reduced by applying the present embodiment, it is possible to accurately calculate the stationary position.

Fifth Embodiment

In the first embodiment, the case of creating a superimposed image at the single slice position, calculating a stationary position based on the superimposed image, and determining a stationary phase based on the stationary position has been described. In the present embodiment, a superimposed image is created at a plurality of slice positions, a stationary position and a stationary phase are calculated at each slice position, and the stationary phase of the target organ is determined based on the stationary phase at each slice position. Hereinafter, detailed explanation will be given with reference to FIG. 14.

Figure 14:
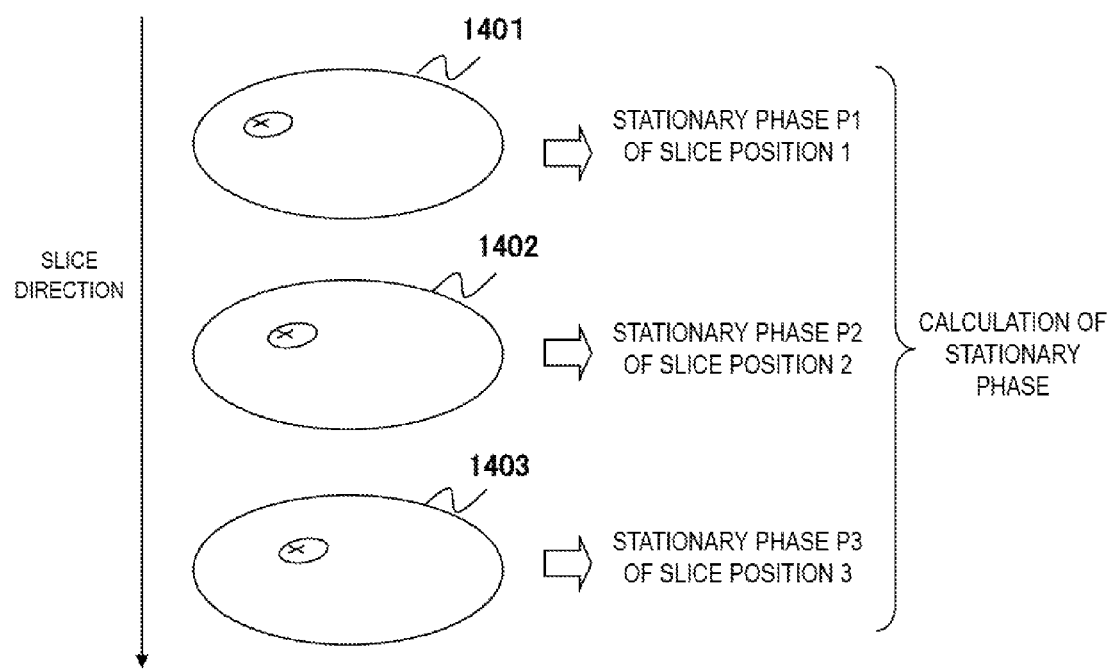
FIG. 14 is a diagram explaining a fifth embodiment of the present invention.

FIG. 14 shows that tomographic images 1401 to 1403 are created for a plurality of slice positions. The tomographic images 1401 to 1403 are tomographic images at slice positions 1 to 3. In the present embodiment, steps 201 to 205 in the first embodiment are executed at each slice position. When executing steps 201 to 205, it is preferable to treat the same organ at each slice position as a target organ. As a result, stationary phases P1 to P3 are calculated at the slice positions 1 to 3.

The system controller 124 determines the stationary phase of the target organ based on the stationary phase calculated for each slice position. For example, the average value of the stationary phases calculated at the respective slice positions is assumed to be the stationary phase of the target organ. In the case of FIG. 14, the average value of the stationary phases calculated at the respective slice positions is the average value (P1+P2+P3)/3 of P1 to P3. Alternatively, a stationary phase at a specific slice position of a plurality of slice positions may be set as the stationary phase of the target organ. For example, a stationary phase at the central slice position of a plurality of slice positions may be set as the stationary phase of the target organ. In the case of FIG. 14, the stationary phase P2 at the slice position 2 is the stationary phase of the target organ.

According to the present embodiment, the stationary phase of the target organ is determined based on the stationary phases at a plurality of slice positions. Therefore, it is possible to obtain a calculation result based on a wider range of information without being limited to the information at a single slice position.

While a plurality of embodiments of the present invention have been described above, the respective embodiments may be appropriately combined.

In addition, the present invention is not limited to the description of the embodiments. Although the system controller 124 causes the image processing device 122 to execute some processing steps of each embodiment in the above explanation, the system controller 124 may execute the processing step.

In addition, although the X-ray CT apparatus has been described as an example of the medical image diagnosis apparatus of the present invention, a magnetic resonance imaging (MRI) apparatus that acquires nuclear magnetic resonance data, which is generated by the nuclear spins in the object placed in a uniform magnetic field, and creates a tomographic image using the acquired nuclear magnetic resonance data is also included in the medical image diagnosis apparatus of the present invention. In the MRI apparatus, the nuclear magnetic resonance data are acquired as the distribution information of the nuclear spins. In addition, in the X-ray CT apparatus, projection data is acquired as the distribution information of the X-ray attenuation material. That is, in medical image diagnosis apparatuses including an MRI apparatus and an X-ray CT apparatus, nuclear magnetic resonance data or projection data is acquired as material distribution information, and the acquired material distribution information is used to create a tomographic image.

REFERENCE SIGNS LIST

1: X-ray CT apparatus
100: scanning gantry unit
101: X-ray tube
102: rotary disk
103: collimator
104: opening
105: bed
106: X-ray detector
107: data acquisition system
108: gantry controller
109: bed controller
110: X-ray controller
120: console
121: input device
122: image processing device
123: storage device
124: system controller
125: display device
130: movement information measuring device
301: electrocardiographic information
302: projection data
303-1 to 303-3: tomographic images of different cardiac phases
304: superimposed image
401: superimposed image
402: trajectory of target organ
403: stationary position
601: image display portion
602: phase display portion
603: distance display portion
801: tomographic image
802: region of interest
1401: tomographic image of slice position 1
1402: tomographic image of slice position 2
1403: tomographic image of slice position 3

The invention claimed is:

1. A medical image diagnosis apparatus, comprising:
a storage unit that stores material distribution information, which is acquired from an object including a target organ that moves periodically, and movement information, which is measured together with the material distribution information;
an image reconstruction unit that reconstructs a plurality of tomographic images of different movement phases using the material distribution information and the movement information;
a superimposed image creation unit that creates a superimposed image by superimposing the plurality of tomographic images;
a specific position calculation unit that calculates a specific position of the target organ based on the superimposed image; and
a specific phase determination unit that determines a specific phase of the target organ based on the specific position.

2. The medical image diagnosis apparatus according to claim 1, further comprising:
a display unit that displays a marker, which indicates the specific position calculated by the specific position calculation unit, together with any one of the plurality of tomographic images or the superimposed image.

3. The medical image diagnosis apparatus according to claim 2,
wherein the display unit displays a plurality of tomographic images selected from the plurality of tomographic images together with the marker.

4. The medical image diagnosis apparatus according to claim 1,
wherein the superimposed image creation unit includes a weighting factor setting section that sets a weighting factor corresponding to the movement phase and a weighted tomographic image creation section that creates a plurality of weighted tomographic images by multiplying each of the plurality of tomographic images by the weighting factor, and creates the superimposed image by superimposing the plurality of weighted tomographic images.

5. The medical image diagnosis apparatus according to claim 4,
wherein the weighting factor setting section sets the weighting factor based on a time density curve acquired by a monitoring scan performed before contrast imaging.

6. The medical image diagnosis apparatus according to claim 1,
wherein the superimposed image creation unit includes an interpolation image creation section that creates an interpolation image between adjacent tomographic images of the plurality of tomographic images, and creates the superimposed image using the plurality of tomographic images and the interpolation image.

7. The medical image diagnosis apparatus according to claim 1,
wherein the superimposed image creation unit includes an average image creation section that creates an average image of the plurality of tomographic images using the superimposed image and a difference image creation section that creates a difference image between the average image and any one of the plurality of tomographic images, and
the specific position calculation unit calculates the specific position of the target organ using the difference image.

8. The medical image diagnosis apparatus according to claim 1,
wherein the image reconstruction unit reconstructs a plurality of tomographic images of different movement phases for different slice positions,
the superimposed image creation unit creates a superimposed image for different slice positions, the specific position calculation unit calculates the specific position of the target organ for different slice positions, and the specific phase determination unit calculates a specific phase for different slice positions, and determines the specific phase of the target organ based on the specific phase calculated for different slice positions.

9. The medical image diagnosis apparatus according to claim 1, wherein the material distribution information is projection data or nuclear magnetic resonance data acquired from the object.

10. A phase determination method using a medical image diagnosis apparatus, comprising:

an image reconstruction step of reconstructing a plurality of tomographic images of different movement phases using material distribution information, which is acquired from an object including a target organ that moves periodically, and movement information, which is measured together with the material distribution information;

a superimposed image creation step of creating a superimposed image by superimposing the plurality of tomographic images;

a specific position calculation step of calculating a specific position of the target organ based on the superimposed image; and a specific phase determination step of determining a specific phase of the target organ based on the specific position.

* * * * *